(12) United States Patent
Schermeier et al.

(10) Patent No.: US 7,532,930 B2
(45) Date of Patent: May 12, 2009

(54) CARDIAC PACEMAKER

(75) Inventors: Olaf Schermeier, Berlin (DE); Wolf Worzewski, Berlin (DE)

(73) Assignee: Biotronik CRM Patent AG (DE)

( * ) Notice: Subject to any disclaimer, the term of this patent is extended or adjusted under 35 U.S.C. 154(b) by 613 days.

(21) Appl. No.: 11/095,941

(22) Filed: Mar. 31, 2005

(65) Prior Publication Data

US 2005/0222630 A1 Oct. 6, 2005

(30) Foreign Application Priority Data

Apr. 1, 2004 (DE) ............ 10 2004 017 137

(51) Int. Cl.
*A61A 1/39* (2006.01)
(52) U.S. Cl. ............... 607/28; 607/9; 607/14; 607/17; 607/27
(58) Field of Classification Search ........... 607/9, 607/28, 14, 17, 27
See application file for complete search history.

(56) References Cited

U.S. PATENT DOCUMENTS

| | | | |
|---|---|---|---|
| 4,974,589 A * | 12/1990 | Sholder | 607/9 |
| 5,103,820 A * | 4/1992 | Markowitz | 607/9 |
| 5,247,929 A | 9/1993 | Stoop et al. | |
| 5,395,396 A * | 3/1995 | Lindgren et al. | 607/9 |
| 5,466,245 A * | 11/1995 | Spinelli et al. | 607/17 |
| 5,601,615 A * | 2/1997 | Markowitz et al. | 607/28 |
| 5,683,426 A * | 11/1997 | Greenhut et al. | 607/9 |
| 5,735,881 A | 4/1998 | Routh et al. | |
| 5,861,012 A | 1/1999 | Stroebel | |
| 6,192,274 B1 * | 2/2001 | Worzewski | 607/14 |
| 6,345,201 B1 * | 2/2002 | Sloman et al. | 607/28 |
| 6,389,316 B1 | 5/2002 | Bornzin et al. | |
| 6,434,428 B1 | 8/2002 | Sloman et al. | |
| 6,584,354 B1 | 6/2003 | Mann et al. | |
| 2003/0195579 A1 * | 10/2003 | Bradley et al. | 607/27 |
| 2004/0030358 A1 | 2/2004 | Rueter et al. | |
| 2005/0021095 A1 | 1/2005 | Rueter et al. | |

FOREIGN PATENT DOCUMENTS

| | | |
|---|---|---|
| EP | 0 705 620 | 4/1996 |
| EP | 0 826 391 | 3/1998 |

* cited by examiner

*Primary Examiner*—Mark W Bockelman
*Assistant Examiner*—Roland Dinga
(74) *Attorney, Agent, or Firm*—Hahn Loeser & Parks LLP (57) ABSTRACT

Certain embodiments of the present invention disclose an electrostimulator, in particular an atrial cardiac pacemaker, comprising electrode connections which are connected to a stimulation unit for the delivery of stimulation pulses by way of the electrode connections, and a stimulation control unit which is connected to the stimulation unit and adapted to trigger the delivery of stimulation pulses and to determine the strength of the stimulation pulses and for that purpose to deliver a stimulation control signal to the stimulation unit, and a detection unit which is connected to the stimulation control unit and at least indirectly to the electrode connections and adapted to evaluate electrical potentials at the electrode connections and to detect intrinsic (natural, spontaneous) events. The stimulation control unit is adapted to produce a far-field signal if the detection unit detects an intrinsic atrial event within a predetermined far-field coupling interval which begins after triggering of a ventricular stimulation pulse.

30 Claims, 5 Drawing Sheets

CARDIAC PACEMAKER

CROSS-REFERENCE TO RELATED APPLICATIONS/INCORPORATION BY REFERENCE

This application claims priority to German patent application serial number 10 2004 017 137.8 filed on Apr. 1, 2004.

TECHNICAL FIELD

Embodiments of the present invention relate to an electrostimulator. In particular, certain embodiments of the present invention concern an implantable electrostimulator for the heart such as an atrial cardiac pacemaker or a dual-chamber cardiac pacemaker in general. Here, the term dual-chamber cardiac pacemaker is used to denote cardiac pacemakers or implantable electrostimulators such as cardioverters or defibrillators, which are adapted to stimulate at least two chambers of a heart, for example the atrium and one or two ventricles.

The electrostimulator has electrode connections which are connected to a stimulation unit for delivering stimulation pulses by way of the electrode connections, and a stimulation control unit which is connected to the stimulation unit and adapted to trigger the delivery of stimulation pulses and to determine the strength of the stimulation pulses and for that purpose to deliver a stimulation control signal to the stimulation unit. The cardiac pacemaker also has a detection unit which is connected to the stimulation control unit and at least indirectly to the electrode connections and is adapted to evaluate electrical potentials at the electrode connections and detect intrinsic events.

Intrinsic events are also referred to as natural or spontaneous events or as intrinsic action and characterize independent contraction of a heart chamber such as an atrium or a ventricle. Heart chambers in the meaning used in this description can thus be both an atrium and also a ventricle.

Certain embodiments of the present invention also concern an atrial capture detector which has at least one signal or data input for signals or data representing cardiac events.

BACKGROUND OF THE INVENTION

It is a usual property of cardiac pacemakers that they can stimulate a heart to perform a contraction by means of electrical stimulation pulses. Depending on the respective structure, setting or programming of the cardiac pacemaker, stimulation pulses are delivered unconditionally at a time which is predetermined by means of a timer—this corresponds to a triggered mode of the pacemaker—or conditionally, that is to say only when no natural contraction of the heart occurs within a predetermined time window (which is usually referred to as the escape interval). The last-mentioned operating mode of the cardiac pacemaker is referred to as the inhibited mode because the detection of a natural contraction of the heart (which can be recognized as a so-called intrinsic event in an electrocardiogram (ECG) within the escape interval leads to inhibition of the delivery of a stimulation pulse.

In regard to the escape intervals, a distinction is drawn for example between atrial and ventricular escape intervals, more specifically depending on whether this involves triggering atrial stimulation pulses for delivery to the atrium of a heart or triggering of ventricular stimulation pulses which are to be delivered to the ventricle. In particular, the delivery of ventricular stimulation pulses, in so-called AV sequential cardiac pacemakers, is controlled in such a way that a ventricular escape interval (also referred to as the AV interval) is started by an atrial event. The ventricular escape or AV interval is of a duration which approximately corresponds to the duration of a natural stimulation conduction from the atrium to the ventricle. Frequently the AV interval is set somewhat longer in order to prevent a stimulation pulse preceding a natural contraction or indeed coinciding with a simultaneous natural contraction. In the last-mentioned case (coincidence of natural and stimulated contraction), that is referred to as fusion events (referred to in English as fusion beats). Such a prolongation of the AV interval is also referred to as hysteresis.

Besides natural transconduction of stimuli from the atrium to the ventricle, there may also be a stimulus conduction from the ventricle to the atrium, which is referred to as retrograde, with the consequence that a ventricular contraction triggers an atrial contraction by retrograde stimulus conduction with a corresponding delay. In general such an atrial event which is based on retrograde conduction is premature from physiological points of view and, in connection with cardiac pacemakers, can result in a pacemaker-induced tachycardia, also referred to as pacemaker-mediated tachycardia or PMT.

A further problem is that the far-field of a ventricular stimulus is also to be perceived (detected) in the atrium of a heart. The result of this can be that far-field detection of a ventricular stimulation pulse in the atrium is falsely evaluated as an intrinsic atrial event, that is to say which is involved with a natural contraction. That problem is usually combated by a post-ventricular, atrial refractory time which begins with the triggering of a ventricular stimulus and within which no atrial events are detected or, if admittedly detected, are then at least not evaluated.

Electrostimulators such as, in particular, cardiac pacemakers produce a muscle contraction by the delivery of a sufficiently strong stimulation pulse. In the case of implantable cardiac pacemakers, it is basically desirable if the respective stimulation pulse is just sufficiently strong to sufficiently stimulate the myocardium in the area around the stimulation electrode. That stimulus which results in contraction of the myocardium is then propagated in a natural fashion starting from the stimulation point and accordingly results in complete contraction of the respective heart chamber, that is to say atrium or ventricle. That stimulation pulse amplitude which is just sufficient to cause response (capture) of the myocardium to a stimulation pulse is referred to as the stimulation threshold. A stimulation pulse above the stimulation threshold, which causes a contraction of the myocardium, is referred to as superthreshold while a stimulation pulse which does not produce a contraction of the myocardium, below the stimulation threshold, is referred to as subthreshold.

Stimulation pulses which are just of a pulse strength which for safety reasons is above the stimulus threshold require less energy than even stronger stimulation pulses. In consideration of the energy capacity of implanted cardiac pacemakers, which is limited from the outset, the aim is always to detect the respective stimulus threshold at the stimulation location as precisely as possible in order to be able to adapt the pulse strength or amplitude of a stimulation pulse to the respectively current stimulus threshold as precisely as possible. The stimulus threshold can change in the course of time and therefore a one-off stimulus threshold test upon implantation is generally not sufficient.

It is therefore known for cardiac pacemakers to be provided with means for stimulation success checking, with which it is possible to determine whether a delivered stimulation pulse has resulted in a response on the part of the myocardium and has produced a corresponding stimulus response.

(Direct) automatic determination of the presence (absence) of a stimulus response after a stimulation pulse by virtue of measurement of the evoked potential with the same electrode as that with which the stimulation pulse whose effectiveness is to be checked was delivered has already been implemented for ventricular stimulation pulses. The corresponding principles of such a solution can in principle also apply to the atrium level.

In actual fact however at the present time, for the atrium region, there is no implantable or external system with which fully automatic atrial threshold tracking or fully automatic atrial stimulus threshold determination can be reliably effected.

The lack of availability of a corresponding system for atrial application is no surprise because the evoked potentials in the atrium, by virtue of its muscle mass which is substantially less (in comparison with the ventricle) and because of the differences in the specific stimulus conduction system, are of a signal quality which is substantially worse for detection, than the evoked ventricle potentials.

Approaches for providing an atrial stimulus response or capture detector are known from U.S. Pat. Nos. 5,601,615, 5,861,012 and 6,584,354. Those known approaches are unsatisfactory for various reasons.

Therefore, it is desirable to provide a cardiac pacemaker affording stimulation success checking which is also suitable for the atrium of a heart and which, as far as possible, avoids disadvantages of the state of the art.

SUMMARY OF THE INVENTION

In accordance with certain embodiments of the present invention, such a desire is attained in an electrostimulator of the kind set forth in the opening part of this specification whose stimulation control unit is adapted, for the purposes of stimulation success checking (capture detection) in the atrium to trigger at least one atrial stimulation pulse and to detect stimulation success (capture) in the atrium or ineffective atrial stimulation (non-capture) on the basis of non-detection or detection respectively of at least one possibly occurring intrinsic (natural, spontaneous) atrial event within a predetermined period of time.

The stimulation control unit is adapted, at least for a limited period of time serving in particular for stimulation success checking (capture detection) or a stimulus threshold test, to trigger ventricular stimulation pulses with the expiry of an AV interval which begins with an intrinsic or stimulated atrial event and which is so short that fusion events, that is to say events in respect of which a ventricular stimulation pulse occurs substantially at the same time as a natural ventricular contraction, are avoided.

The stimulation control unit is further adapted to distinguish atrial events which are based on far-field detection of ventricular events in the atrium from intrinsic atrial events insofar as such atrial events which are at a spacing in respect of time with respect to the respectively preceding ventricular stimulation pulse, which at least approximately corresponds to the time spacing between a ventricular stimulation pulse and the corresponding atrial event in an observation period, for example in a preceding cardiac cycle, are evaluated as based on far-field detection and are not counted as intrinsic events.

For that purpose, the stimulation control unit may be adapted to produce a far-field signal characterizing atrial events based on far-field detection, if the detection unit detects an intrinsic atrial event within a predetermined far-field coupling interval which begins after triggering of a ventricular stimulation pulse. The far-field coupling interval may begin between 50 and 100 ms after triggering of the ventricular stimulation pulse and between 150 and 200 ms after triggering of the same ventricular stimulation pulse.

That solution permits a particularly short post-ventricular atrial refractory time so that, in particular, few atrial events are not detected because they fall into the atrial refractory time. The danger, which is increased as a result, of perceiving such atrial events and falsely interpreting them as intrinsic events which are based on the detection of the far-field of ventricular stimulation pulses in the atrium is combated by atrial events which have a typical spacing in respect of time which is characteristic for far-field detection in relation to the preceding ventricular stimulus admittedly being recorded but not being evaluated as intrinsic events.

Certain variant embodiments of the present invention concern the treatment of retrograde stimulus conduction and crosstalk.

In regard to such supposed atrial events which are either based on retrograde stimulus conduction from ventricle to atrium or on crosstalk between the electrode lines, the electrostimulator, according to an embodiment of the present invention, is adapted as follows:

The stimulation control unit is adapted to produce a retrograde stimulus conduction signal if the detection unit detects an intrinsic atrial event within a predetermined time interval after triggering of a ventricular stimulation pulse. The predetermined time interval in that case may be given by a coupling interval of between 180 ms and 350 ms between triggering of the ventricular stimulation pulse and detection of the intrinsic atrial event.

Alternatively, or additionally, the stimulation control unit is adapted to produce a Loss-of-Capture signal (LOC) if the ratio of the number of retrograde stimulus conduction signals to the number of triggered ventricular stimulation pulses within a predetermined period of time exceeds a predetermined threshold value of between 0.5 and 1. The predetermined threshold value may be, for example, 0.8.

Alternatively, or additionally, the stimulation control unit is adapted to produce a crosstalk signal if the detection unit detects an intrinsic atrial event within a predetermined time window beginning with triggering of a respective ventricular stimulation pulse. The predetermined time window may be of a duration of between 30 ms and 70 ms, and particularly may be, for example, 50 ms.

In accordance with an embodiment of the present invention, a particular electrostimulator has a detection unit adapted to detect as intrinsic events only such atrial events with which no crosstalk signal or no far-field signal is to be associated.

An alternative or supplemental solution to the problem of stimulation success checking in the atrium is afforded by an electrostimulator of the kind set forth in the opening part of this specification, having a stimulation control unit which additionally, or alternatively, to the above-outlined features is adapted:

- over a predetermined period of time including a plurality of cardiac cycles to trigger stimulation pulses at a set stimulation rate in a triggered mode (T-mode) in which the delivery of stimulation pulses is not inhibited even in the case of the occurrence of intrinsic events in the stimulated chamber, and
- for the predetermined period of time to detect possibly occurring intrinsic (natural, spontaneous) events, and for the predetermined period of time to ascertain the presence or absence of a natural cardiac rhythm on the basis of the detected or non-detected intrinsic (natural, spontaneous) events.

The stimulation control unit may be adapted, on the basis of a stimulation rate applied prior to the predetermined period of time including a plurality of cardiac cycles, to set the stimulation rate during the predetermined period of time including a plurality of cardiac cycles in such a way that the set stimulation rate is greater than the previously applied stimulation rate. During the predetermined period of time including a plurality of cardiac cycles therefore superstimulation may take place, more specifically at a stimulation rate which is increased by about 10 ppm (pulses per minute) in relation to the previously applied rate.

For that purpose it is not necessary to ascertain a natural heart rate which obtains prior to the predetermined period of time including a plurality of cardiac cycles. That does not exclude the stimulation rate applied prior to the predetermined period of time including a plurality of cardiac cycles being based on a natural heart rate which is ascertained together with the detection unit.

Alternatively, however, the set stimulation rate used can also be that stimulation rate which occurs at the beginning of the predetermined period of time, that is to say it is not absolutely necessary to set a higher rate if for example the previously applied rate is already increased because of physical activity on the part of the patient or for other reasons.

It is to be noted that embodiments of the present invention presented herein do not require measurement of the evoked potential and therefore avoids on the one hand the technical complication and expenditure linked to such measurement and on the other hand avoids certain disadvantages involved in a method which is based on checking only for a short time after the pulse whether there is an evoked potential (U.S. Pat. No. 5,601,615), in which however the interaction between stimulation and the intrinsic rhythm (natural cardiac rhythm) is disregarded. Those disadvantages include uncertainties which, in the previous approaches, under certain conditions, can result in limited sensitivity and/or specificity of the algorithm for automatic detection of the atrial stimulus response (for example in the case of an atrial fusion systole or in the event of excessively high polarization voltage after pulse delivery).

Embodiments of the present invention are, therefore, not reliant on problematical measurement of evoked signals after the individual atrium pulses (atrial stimulation pulses), but for effectiveness checking (capture control) of atrium stimulation judges the effects thereof on the atrial intrinsic rhythm (natural cardiac rhythm) during a given time window (predetermined period of time): ineffective atrium stimulation has no influence on the atrium rhythm and means that an intrinsic atrium rhythm occurs and can be registered by the pacemaker by means of markers for atrial sense events. In comparison the intrinsic atrium rhythm (natural cardiac rhythm or intrinsic rhythm in the atrium) may be suppressed by effective atrium stimulation at a frequency (set stimulation rate) which is greater than the atrial intrinsic frequency (natural heart rate) and cannot occur, which can be established by an absence of atrial sense events (detected intrinsic atrial events).

In cases in which there are doubts about the atrial pulse response (atrial capture), stimulation can be effected for example in the DDD mode with a derived or set stimulation frequency which is about 10 ppm (pulses per minute) higher than an atrial intrinsic frequency which was established previously, for example during the atrial detection test.

The electrostimulator may be in the form of an atrial cardiac pacemaker, the stimulation unit is adapted for producing and delivering atrial stimulation pulses, the detection unit for detecting intrinsic atrial events and the stimulation control unit for ascertaining a natural atrial cardiac rhythm on the basis of intrinsic events detected by the detection unit in the atrium. This variant takes account of the fact that the stimulus response detector presented here is basically also suitable for detecting a ventricular stimulation success but it is also suitable in particular for atrial stimulation success checking.

In this respect the stimulation control unit may be adapted, in the predetermined period of time including a plurality of cardiac cycles, to trigger atrial stimulation pulses at a set stimulation rate in a triggered mode in which atrial stimulation pulses are not inhibited, and to trigger ventricular stimulation pulses at a set stimulation rate in a demand mode in which ventricular stimulation pulses are inhibited if intrinsic ventricular events are detected within a respective ventricular escape interval. The particular advantage of that electrostimulator is that unimpaired stimulation of the ventricle can take place while at the same time atrial stimulation success checking, an atrial stimulus threshold test or indeed automatic adaptation of the atrial stimulation pulse strength on the basis of the atrial stimulation success checking can occur.

For atrial stimulation success checking, the atrial stimulus threshold test or automatic adaptation of the atrial stimulation pulse strength, the stimulation control unit may be adapted to ascertain the presence or absence of a natural cardiac rhythm in dependence on whether and/or how many intrinsic events are detected by the detection unit within the predetermined period of time. That detection criterion is particularly simple to implement and is already sufficiently informative.

In addition, in accordance with a certain variant embodiment of the present invention, the stimulation control unit is adapted, for ascertaining the presence or absence of a natural cardiac rhythm, to take account of blanking times in which possibly occurring natural events cannot be detected. That can be effected for example by a fraction of an intrinsic event being overall uniformly counted for the blanking time, more specifically in accordance with the probability of an intrinsic event, on the assumption of a regular natural rhythm, occurring in the blanking time. If for example an actually detected intrinsic event is counted with '1', then, depending on the respective length of the blanking times and the value of the assumed natural rate, for each blanking time, a value of '0.3' can be counted in the period of time involved.

In this connection the stimulation control unit can be adapted to reconstruct a natural cardiac rhythm on the basis of detected natural events having regard to non-detected natural events which potentially occur in the blanking times, and to produce a signal characterizing a natural rhythm if the detected natural cardiac events are to be associated with a regular natural cardiac rhythm.

An embodiment which is advantageous because it is simple to implement is afforded if the detection unit is adapted, for each detected intrinsic event, to produce a sense marker signal in relative time association in relation to the time of the occurrence of the event. The stimulation control unit may then be adapted to produce a respective pace marker signal for each stimulation pulse which is actually triggered, and to ascertain the presence of a natural cardiac rhythm on the basis at least of the sense marker signals or additionally the pace marker signals.

A particular embodiment of an electrostimulator with automatic adaptation of stimulation pulse strength is afforded if the stimulation control unit is adapted to determine a stimulation control signal for stimulation strength in dependence on whether the presence or absence of a natural cardiac rhythm is ascertained within the predetermined period of time. For that purpose the stimulation control unit may be adapted to produce a stimulation control signal which causes an increase in the pulse strength of a stimulation pulse when the presence of a natural cardiac rhythm is ascertained within the predetermined period of time.

An electrostimulator whose stimulation control unit is adapted to determine a capture control signal in dependence on whether the presence or absence of a natural cardiac rhythm is ascertained within the predetermined period of time and additionally or alternatively to produce a Loss-of-Capture signal (LOC) in the case of the presence of a natural cardiac rhythm within the predetermined period of time already affords the advantage of effective stimulation success checking.

The underlying method of embodiments of the present invention can also be used if only a surface ECG is available for analysis (without IEGM/marker registration) and evoked P-waves cannot be clearly recognized. The ineffectiveness of atrium stimulation is then recognized from the fact that, with otherwise AV-sequential stimulation (so-called AV sequences), at more or less regular intervals, chamber pulses are recorded, which had to have been triggered by atrial sense events (so-called PV sequences). In that case PV sequences occur whenever an atrial sense event is perceived outside the atrial refractory period (ARP). Analysis is substantially facilitated by simultaneous registration of a surface ECG with atrial sense markers within and outside the ARP because in that way all spontaneous atrium depolarization effects are detected, besides those which occur in the atrial blanking time which is started by an atrium pulse (so-called in-channel blanking) or by a chamber pulse (so-called cross-channel blanking) and therefore cannot be perceived.

That registration generally makes it possible to clearly demonstrate the existence of an atrial intrinsic rhythm which is not suppressed by atrium stimulation which therefore must be ineffective.

Embodiments of the present invention take advantage of those relationships and sets forth an algorithm which infers the effectiveness of atrium stimulation from the absence of atrial sense events during a (optionally programmable) time window.

In accordance with a certain variant embodiment of the present invention, in this respect the (automatic) atrial detection test is combined with (automatic) testing of the atrial pulse response.

In a first phase an atrial detection test is performed, which serves four purposes. The following are to be established:
1. whether the patient has an atrial intrinsic rhythm,
2. how high the frequency thereof is,
3. whether the programmed atrium sensitivity is sufficient to detect the atrial intrinsic actions, and
4. whether, with the programmed atrium sensitivity and duration of the atrial blanking time (far-field blanking) atrium detection of the QRS complex (so-called far-field-R-detection, 'crosstalk') takes place.

Following the atrial detection test, testing of the atrial pulse response can be effected in a second phase. If, in the atrial detection test which for example in the VDD mode is carried out with a low basic frequency of for example 40 ppm and with a short AV time of for example 100 ms, a regular atrial intrinsic frequency of between 40/min and 100/min is measured, the test phase for testing the atrial pulse response is effected. For that test phase, a certain application involves using the DDD-mode with an atrial refractory time of 775 ms (so that atrial sense events cannot occur outside the atrial refractory time and start an AV time), a basic frequency which is about 20% higher than the previously measured atrial intrinsic frequency, and an AV time of 150 ms (which should not be longer so that in the event of blocking, in the proximal AV node, VA conduction cannot occur). In that second test phase, after four stimulation cycles the time window (comprising n, at least 8, cycles) for measurement of the intervals between the atrial sense events is started and the resulting events are evaluated as follows:

if no or only an atrial sense event is registered, the atrium stimulation is deemed to be effective;

if at least three intervals between the atrial sense events are identical to those measured in the atrial detection test (plus/minus tolerance of 50 ms-100 ms which is ideally frequency-dependent), atrium stimulation is deemed to be ineffective and it is assumed that no VA conduction took place after ineffective atrium stimulation;

if regular atrial sense events occur with a fixed coupling in the region of about 180 ms-300 ms after the ventricular stimulus, atrium stimulation is also deemed to be ineffective and it is assumed that VA conduction took place after the ineffective atrium stimulation;

otherwise (that is to say in the case of two or more atrial sense events whose intervals do not satisfy the above-mentioned conditions), it is assumed that no clear information can be provided about the ineffectiveness or effectiveness of atrium stimulation; the user must then analyze the documentation of the test in order to find out the cause of the ambiguous test result. The lack of clarity can be caused in that case for example by atrial extrasystoles or an atrial exit block which occurs only intermittently.

Alternative Frequency Analysis:

In order to enlarge the time window for detection and evaluation of the atrial signals, as an alternative to the method described in the five preceding paragraphs, the described method can also be executed in the context of a frequency analysis. That too is capable of filtering out the atrial sense events caused by crosstalk and far-field so that it is also possible to take account of measurable signals within the atrial blanking time after a ventricular stimulation pulse Vp (PVARP: post-ventricular atrial blanking period). If no signals which involve retrograde transconduction from the ventricle to the atrium should be found, that frequency analysis is performed with all twos-combinations of the signals atrially detected in the period being investigated. In that respect the intervals between all twos-combinations of signals are filtered with a band pass. That passes frequencies in the range basic_rate+−tolerance. Any signal which that filter passes in at least one combination is classified as a non-intrinsic signal as there is a high degree of probability that it is to be attributed to stimulation in the atrium or the ventricle. Conversely any signal which does not pass that filter is classified as intrinsic action.

If the atrial intrinsic rhythm in the preceding detection test was found to be stable, an identical frequency analysis procedure can be used for checking the signals classified as intrinsic action for consistency with that intrinsic rhythm. It will be noted in this respect that it must be borne in mind that individual intrinsic actions are not recorded, by virtue of analog blanking. Therefore, when designing the band pass filter, besides the intrinsic rhythm, the corresponding low-grade subharmonic frequencies are also to be taken into consideration.

The second test phase for determining the atrial stimulus threshold:

If in a particular embodiment of all electrostimulators or methods described herein the atrial stimulus threshold is to be determined, the described second test phase (for testing effectiveness of atrium stimulation) is so frequently repeated with a respectively decremented level of atrial pulse energy, until a clearly effective pulse response becomes a clearly ineffective pulse response or a clear finding cannot be made in accordance with the foregoing criteria.

In order to ensure rapid attainment of the stimulus threshold alternatively the amplitude can also not be decremented in constant 0.1 V steps but can be determined with the following formula:

If the previous stimulus is effective:

$$\mathrm{Amp}(t+1) = \mathrm{Amp}(t) - abs(\mathrm{Amp}(t) - \mathrm{Amp}(t-1))/2$$

If the previous stimulus is ineffective:

$$\mathrm{Amp}(t+1) = \mathrm{Amp}(t) + abs(\mathrm{Amp}(t) - \mathrm{Amp}(t-1))/2$$

That control of amplitude means that the stimulus threshold is reached with a starting amplitude of for example 3.6 V, within a maximum of 6 measurements. The lowest atrial pulse energy at which an atrial pulse response can be established then applies as the atrial stimulus threshold.

BRIEF DESCRIPTION OF SEVERAL VIEWS OF THE DRAWINGS

The invention will now be described in greater detail by means of an embodiment with reference to the Figures in which.

DETAILED DESCRIPTION OF THE INVENTION

Figure 1:
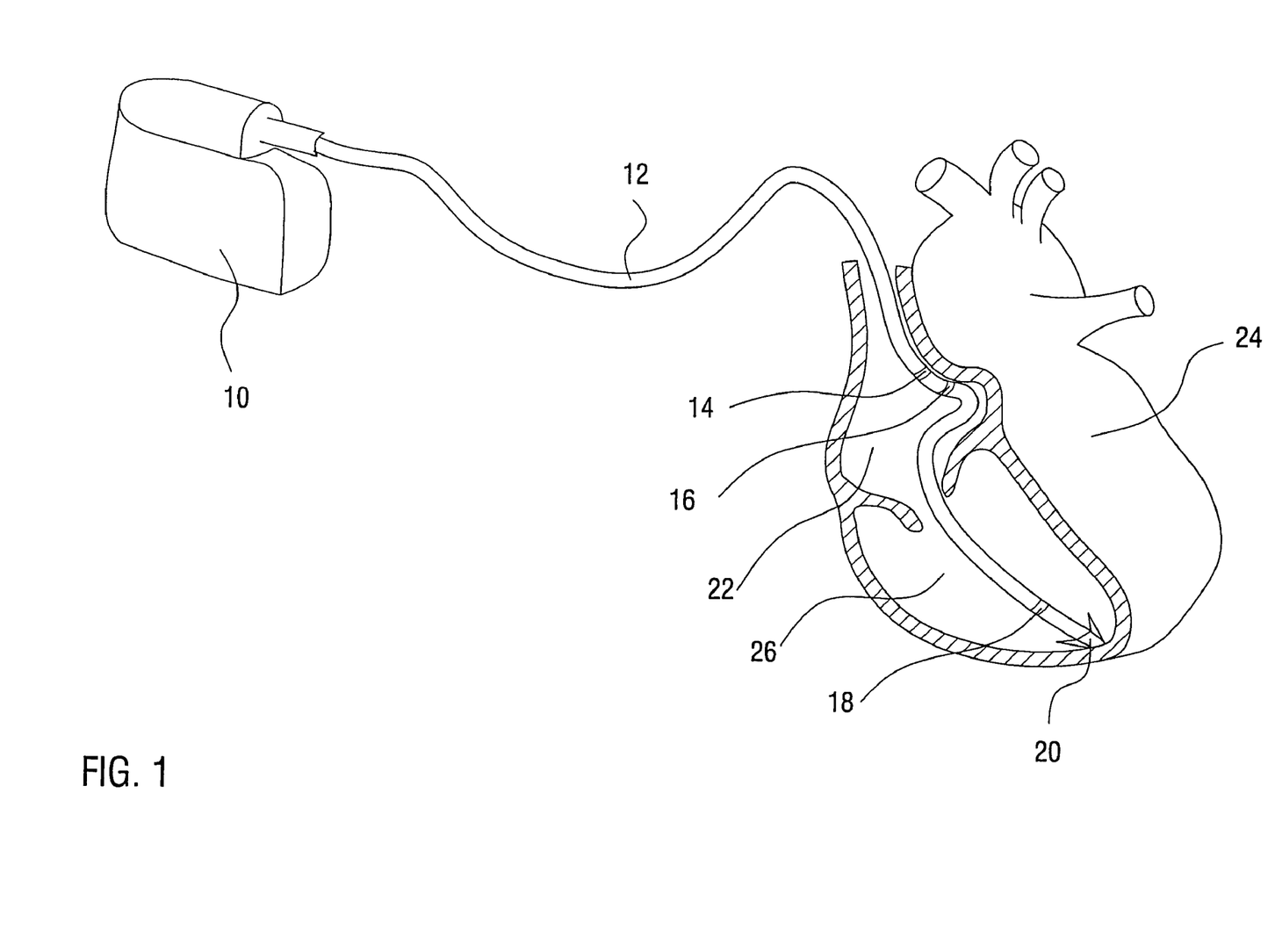
FIG. 1 shows a diagrammatic view of a dual-chamber cardiac pacemaker with electrodes for the atrium and the ventricle of a heart, in accordance with an embodiment of the present invention.

FIG. 1 shows as an implantable stimulation device, a cardiac pacemaker 10, to which is connected an electrode line 12 which has two atrial electrodes 14 and 16 and two ventricular electrodes 18 and 20 in the region of the distal end thereof. In FIG. 1 the atrial electrodes 14 and 16 are arranged in the atrium 22 of a heart 24 while the ventricular electrodes 18 and 20 are arranged in the ventricle 26 of the heart 24. Instead of a common electrode line 12 for atrium and ventricle, it is also possible to provide a respective electrode line with for example two electrodes, for each of the atrium and the ventricle. In the illustrated example the implantable stimulation device is a cardiac pacemaker. The device could equally well be a cardioverter or defibrillator. Equally the cardiac pacemaker 10 could also be in the form of a biventricular cardiac pacemaker with an electrode line for stimulation of the left electrode of a heart.

Figure 2:
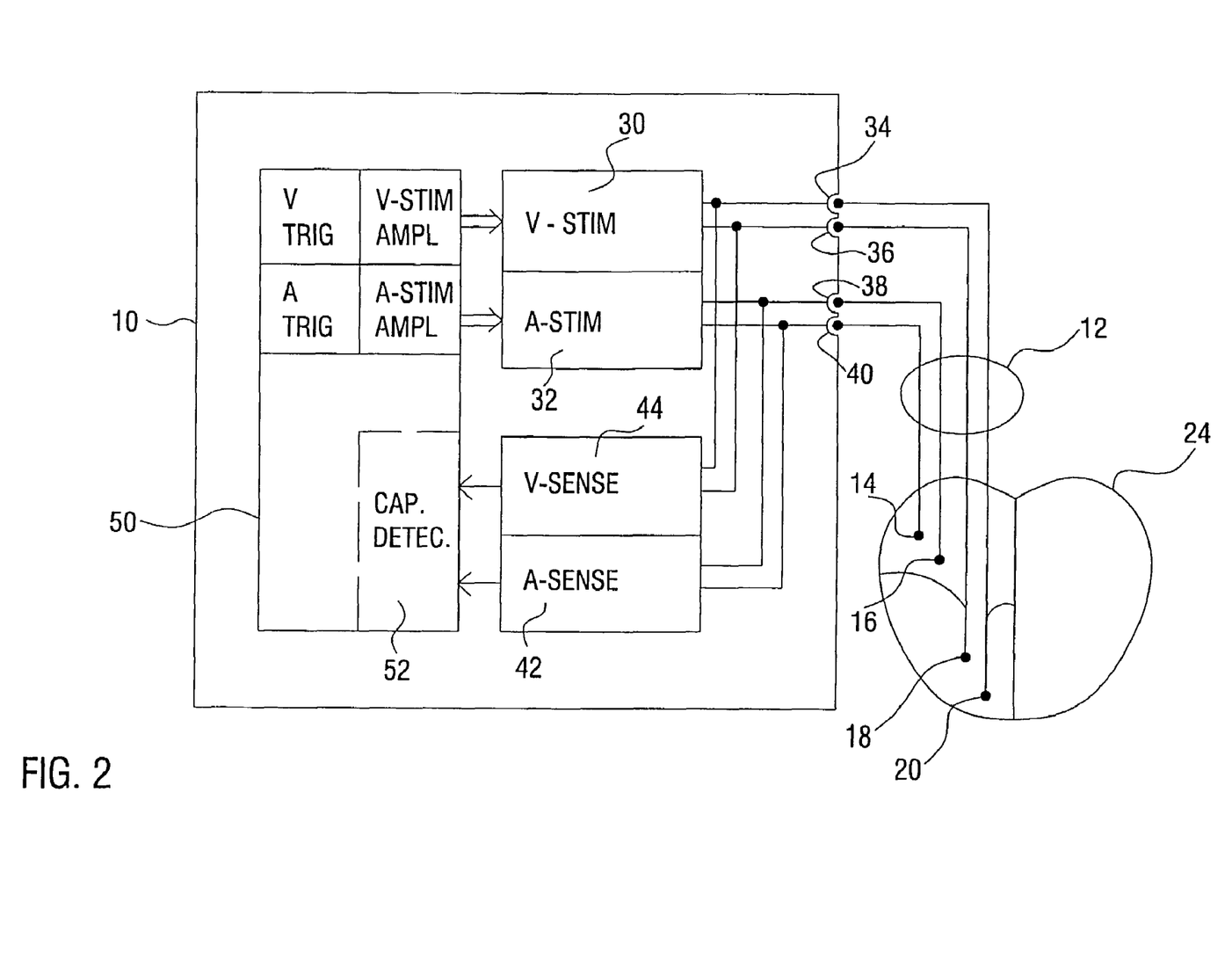
FIG. 2 is a diagrammatic block view of the cardiac pacemaker of FIG. 1 with the components which are used in relation to the function described herein, in accordance with an embodiment of the present invention.

Certain components in the interior of the cardiac pacemaker 10 are a ventricular stimulation unit 30 and an atrial stimulation unit 32 which are each connected by way of two respective ventricular electrode line connections 34 and 36 and two atrial electrode line connections 38 and 40 respectively to the corresponding electrodes 14, 16, 18 and 20 of the electrode line 12.

In addition an atrial input amplifier 42 and a ventricular input amplifier 44 respectively are connected to the electrode line connections 34, 36, 38 and 40. The stimulation units 30 and 32 are so designed that they can deliver stimulation pulses of adjustable stimulation pulse strength by way of the electrode line connections to the corresponding electrodes of the electrode line 12 in the heart 24.

The stimulation units 30 and 32 and the input amplifiers 42 and 44 are respectively connected to a stimulation control unit 50 which for example can be a microprocessor control and has modules for stimulation success detection (capture detection) and for triggering stimulation pulses in the atrium and the ventricle and for setting the appropriate stimulation pulse strength. Accordingly the stimulation control unit 50 has a capture detector 52 in the form of a stimulation success detection module (capture detection module) and a ventricular stimulation pulse triggering unit 54 as well as an atrial stimulation pulse triggering unit 56 and a ventricular stimulation strength unit 58 and an atrial stimulation strength unit 60.

The capture detector 52 is connected to the other modules of the stimulation control unit 50 in such a way that they co-operate in the manner described hereinafter.

The following terminology is used in the context of the following description:

LOC denotes the Loss-of-Capture signal which is produced upon ineffective (atrial) stimulation), CAP denotes a capture signal which is produced in the event of effective (atrial) stimulation, SR denotes the value of the natural heart rate (sine rhythm), PR denotes the respectively current stimulation rate (pacing rate), and $R_{Test}$ denotes the stimulation rate during an (atrial) stimulus threshold test or an automatic atrial stimulation success check.

The performance of the pacemaker shown in FIG. 1 during an automatic atrial stimulation success checking operation or during an atrial stimulus threshold test will now be described, see also FIG. 2:

If the applied stimulation rate PR prior to the predetermined period of time for atrial stimulation success checking is lower than the intrinsic rate SR, that is to say if atrial stimulation pulses are regularly inhibited, the stimulation rate $R_{test}$ which is to be set during the predetermined period of time for the atrial stimulation success checking operation is as follows:

$$R_{test} = SR + 10 \text{ ppm}$$

If the applied stimulation rate PR prior to the predetermined period of time for atrial stimulation success checking is greater than the intrinsic rate SR, that is to say if atrial stimulation pulses are regularly not inhibited but are actually triggered, the stimulation rate $R_{test}$ which is to be set, during the predetermined period of time for atrial stimulation success checking, is as follows:

$$R_{test} = PR + 10 \text{ ppm}$$

During the automatic atrial stimulation success checking operation the following operating parameters are set:

| | |
|---|---|
| Stimulation mode: | DDD |
| Base stimulation rate = | $R_{test}$ |
| Atrio-ventricular delay time (AVD) = | 130 ms; |

That atrio-ventricular delay time avoids ventricular fusion beats and retrograde ventrico-atrial stimulus conduction after effective Ap–Vp

| | |
|---|---|
| Atrial refractory time (ARP) = [ms]; | $60000/R_{test}$ |

The atrio-ventricular delay time is not started after intrinsic depolarization.

| | |
|---|---|
| BiV: | Off; |
| AT prevention: | Off; |
| ALC: | Off; |
| MS: | Off; |
| PMT detection: | Off. |

Figure 3:
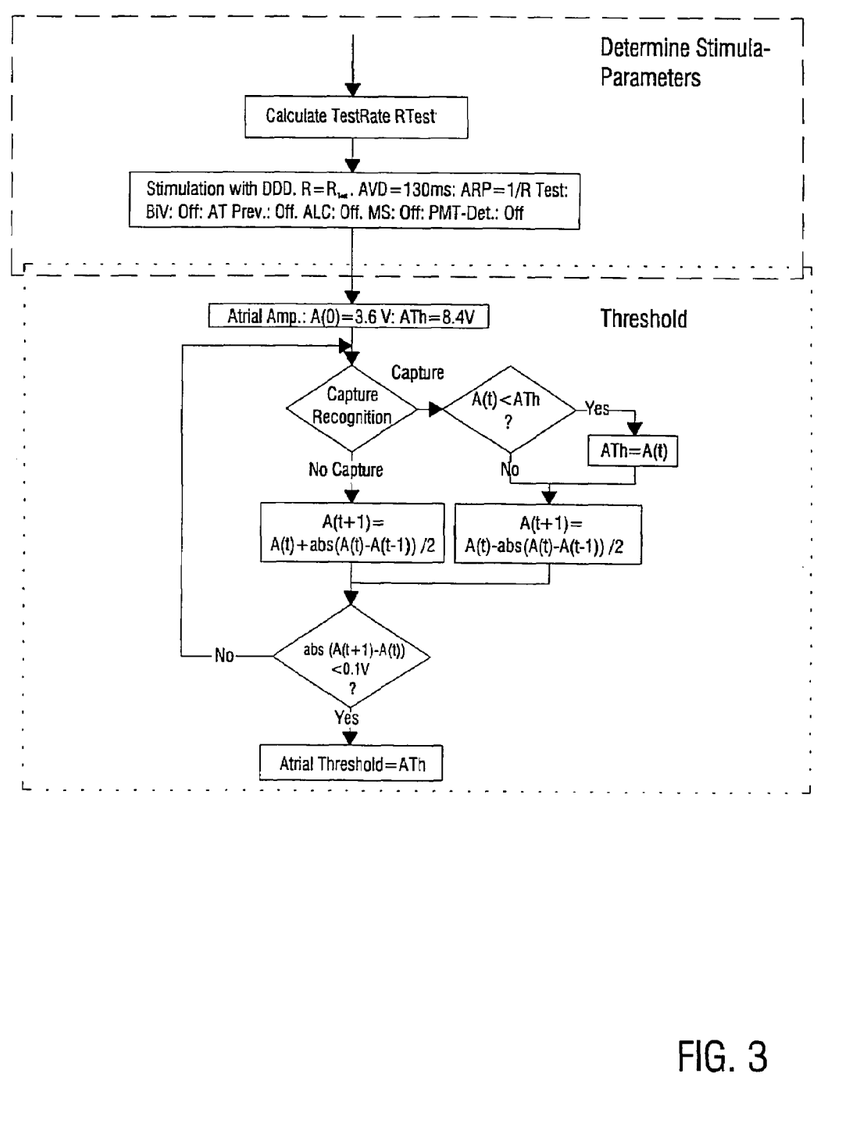
FIG. 3 shows a flow chart reproducing the behavior of the cardiac pacemaker of FIGS. 1 and 2 in the case of automatically determining the atrial stimulus threshold, in accordance with an embodiment of the present invention.

After the stimulation parameters have been established in that way, setting of the atrial stimulation pulse strength is effected (see the block 'threshold' in FIG. 3). The atrial amplitude which predetermines the atrial stimulation pulse strength is fixed at an initial value A (0) of 3.6 volts. In addition a limit value is fixed for the atrial amplitude ATh of 8.4 volts.

Then stimulation success checking (capture recognition) which is described in greater detail hereinafter is effected. If that shows that atrial stimulation was successful (capture), a check is made to ascertain whether the respectively current atrial amplitude A(t) is less than the atrial limit amplitude ATh. If that is the case, the atrial limit amplitude ATh is set equal to the respectively current atrial amplitude A(t). If in contrast the current atrial amplitude A(t) is less than the atrial limit amplitude ATh the previously applicable value for the atrial limit amplitude ATh (for example 8.4 volts) is retained. In both cases, in response to the detection of stimulation success (capture), there is a reduction in the atrial amplitude for the next stimulation step A(t+1), in accordance with the following formula:

$$A(t+1)=A(t)-abs(A(t)-A(t-1))/2$$

If however stimulation success checking (capture recognition) does not show that stimulation success prevails (no capture), there is an increase in the atrial amplitude for the next stimulation step A(t+1), in accordance with the following formula:

$$A(t+1)=A(t)+abs(A(t)-A(t-1))/2$$

After an increase or a reduction in atrial amplitude for the next stimulation step A(t+1), a test is carried out to ascertain whether the absolute value of the change in atrial amplitude is less than 0.1 volt. If that is the case the respectively current atrial limit amplitude ATh is deemed to be the atrial stimulus threshold, otherwise a new stimulus threshold test is carried out with the respectively current atrial amplitude A(t+1) ascertained by the above-described method, more specifically until the absolute value of the change in amplitude is less than 0.1 volt.

Figure 4:
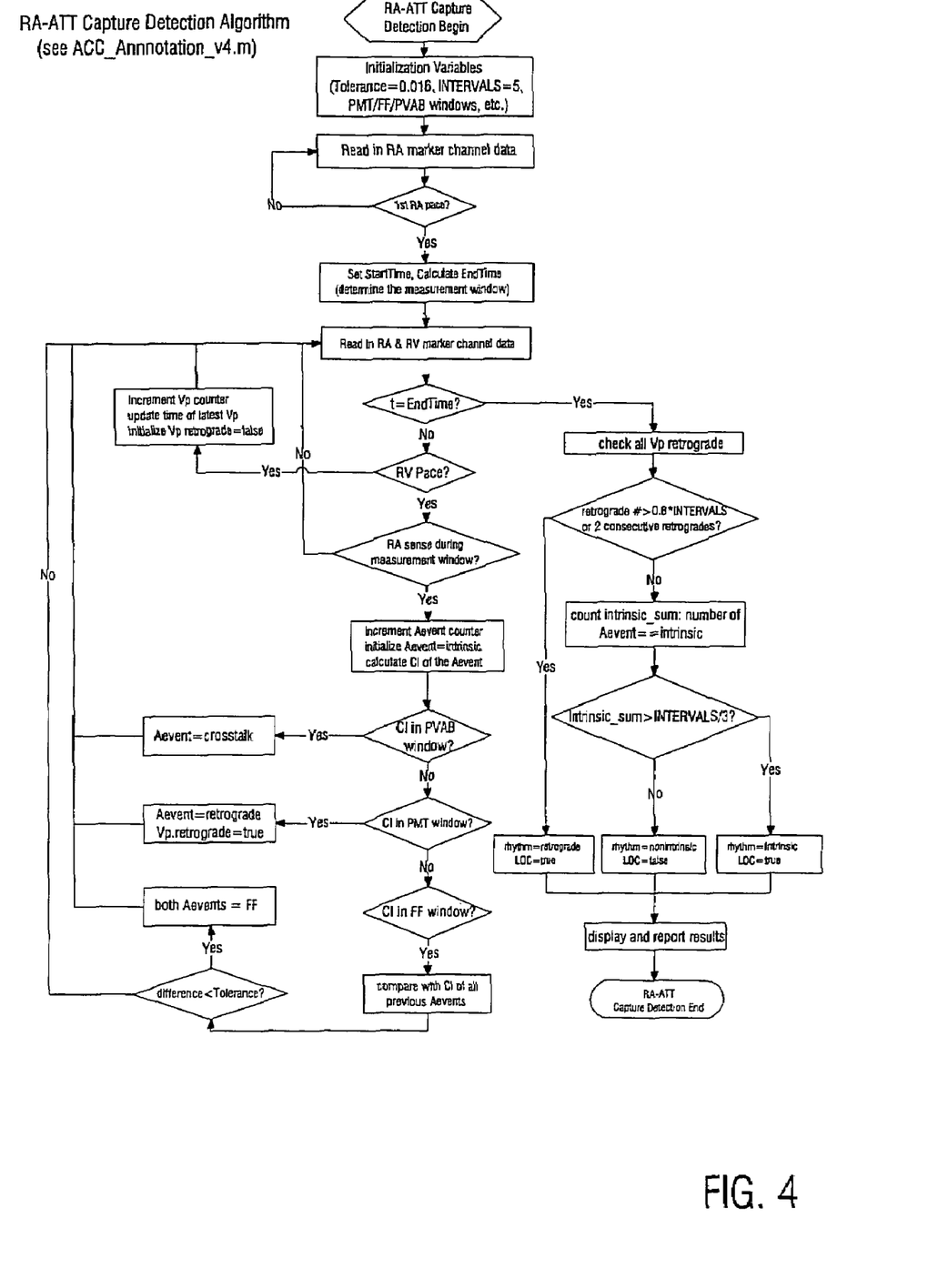
FIG. 4 shows a flow chart which reproduces atrial capture detection of the cardiac pacemaker of FIGS. 1 and 2, in accordance with an embodiment of the present invention.

The details of the mode of operation of the atrial capture detector 52 can be found in the flow chart in FIG. 4.

The atrial stimulation success check (atrial capture detection) shown in the flow chart of FIG. 4 uses a capability of the cardiac pacemaker described herein, more specifically to detect and represent atrial and ventricular events in the form of stimulation events and sense events (detected atrial and ventricular contractions) and the respective moment at which an event occurs. A marker is associated with each event, on a time line. The time sequence of the events can be easily recognized on the basis of the respective markers.

The procedure involved in the atrial stimulation success checking operation in accordance with the flow chart of FIG. 4 is as follows:

Firstly the following variables are initialized, more specifically a tolerance value for a capture interval which reflects the period of time between a right-ventricular stimulation pulse and an atrial event. The tolerance value serves for recognition, which will be further described hereinafter, of such atrial events which are based on far-field detection of ventricular stimulation pulses. In addition a number of intervals is predetermined, which is set for example at 5. In addition the following time intervals, namely PMT intervals, far-field intervals and post-ventricular atrial blanking time (PVAB) are to be predetermined.

After that initialization operation, a search is conducted in the right-atrial marker channel for a first right-atrial stimulation event (right-atrial stimulation pulse). Therewith a measurement time window is started for atrial stimulation success checking.

Within that measurement time window, a check is firstly made to ascertain whether the end time of the measurement time window is reached. If so, final evaluation of stimulation success checking is effected, if not, the marker channel is checked to ascertained whether there is a right-ventricular stimulation event (the terms stimulation event and stimulation pulse are used synonymously in connection with the description relating to FIG. 5). With each existing right-ventricular stimulation pulse, firstly a counter for right-ventricular stimulation pulses Vp is increased by 1 and a check is made to ascertain whether there is a right-atrial sense event within the measurement window. If that is the case, an atrial event counter is increased by 1 and a capture interval is calculated for that atrial event. The capture interval CI is the spacing in respect of time between the previously detected right-ventricular stimulation event and the right-atrial sense event which is detected thereupon. A check is then made to ascertain whether the capture interval is within the post-ventricular atrial blanking time, that is to say whether the detected atrial event is within the post-ventricular atrial blanking time emanating from the right-ventricular stimulation pulse. If that is the case the detected atrial event (Aevent) is categorized as a crosstalk event insofar as the value 'crosstalk' is allocated to a variable Aevent.

If the capture interval is not in the post-ventricular atrial blanking time PVAB, a check is made to ascertain whether the capture interval—that is to say the detected atrial event—is in a PMT interval. If that is the case the atrial event is categorized as an event due to retrograde stimulus conduction, by the value 'retrograde' being allocated to the variable Aevent. The previously detected ventricular stimulation pulse is also classified as 'retrograde'.

If the capture interval does not end either in the post-ventricular atrial blanking time or in the PMP interval, a check is made to ascertain whether the capture interval ends in the far-field interval (FF window), that is to say whether the detected atrial event is in the far-field interval. If that is the case the capture interval is compared to all preceding capture intervals of the previously detected atrial events. If at least two of those capture intervals differ by a period of time which is less than the previously established tolerance value, the two atrial events belonging to the corresponding capture intervals are categorized as being based on far-field detection (FF), by the value 'far-field' or 'FF' being allocated to the variable Aevent.

When the measurement time window is ended, that is to say when initial checking has shown that the end time of the measurement time window is reached, evaluation of the stimulation success checking procedure is effected. For that purpose, firstly the number of detected ventricular stimulation events classified as 'retrograde' is ascertained and a check is made to determine whether it is greater than 0.8 times the previously established number of intervals or whether there are two immediately successive ventricular stimulation pulses classified as 'retrograde'. If one of both or both is the case, a variable rhythm is set to 'retrograde'. In addition a Loss-of-Capture signal (LOC) is produced by a variable LOC being set to 'true'.

If neither of the two above-mentioned conditions in respect of the detected ventricular stimulation events is satisfied, the number of detected intrinsic atrial events is determined; these are all those atrial events detected in the measurement time window, which are not categorized as 'crosstalk', 'retrograde' or 'far-field'. If the number of intrinsic atrial events is greater than the interval value (intervals), divided by 3, the value 'intrinsic' is associated with the variable rhythm. At the same time the variable Loss-of-Capture (LOC) is set to 'true', that is to say a Loss-of-Capture signal is produced.

If the sum of the intrinsic atrial events is smaller than or equal to the number of intervals divided by 3, the variable 'rhythm is set to 'non-intrinsic' and the variable LOC is set to 'not true'. That case characterizes successful atrial stimulation in which an intrinsic atrial rhythm is suppressed.

After those testing operations in the context of evaluation of atrial stimulation success checking, the result, that is to say the value of the respective variable 'rhythm' and the variable LOC, is output.

Figure 5A:
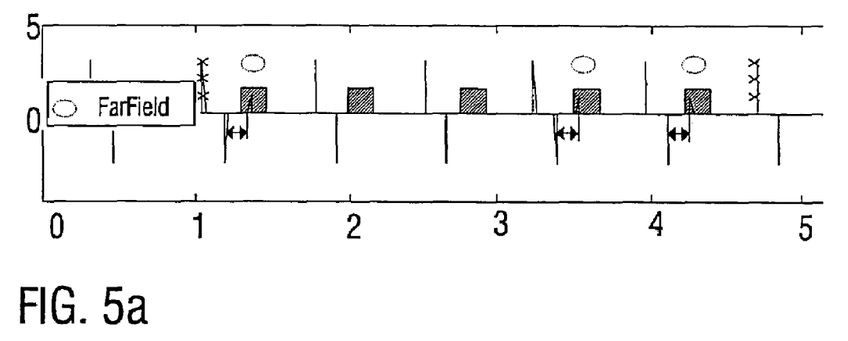
FIGS. 5a and 5b show time-event diagrams reflecting the behavior of the cardiac pacemaker of FIG. 1 in the case of far-field detection of ventricular events in the atrium, in accordance with an embodiment of the present invention.
Figure 5B:
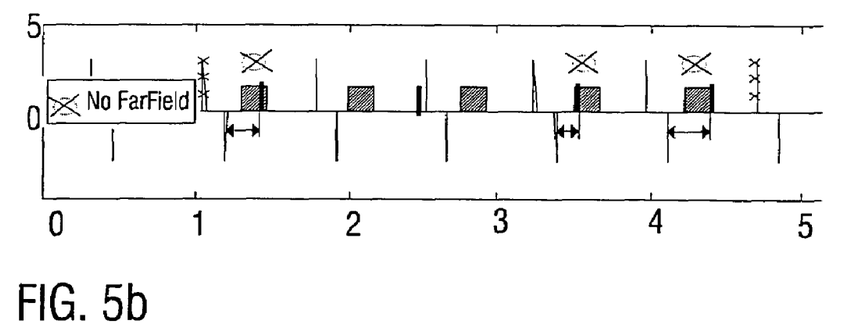

FIGS. 5a and 5b, on the basis of the time-event diagrams illustrated therein, represent detection of such atrial events which are based on far-field detection. Shown above the horizontal center line of each respective diagram in light gray is the respective far-field interval in which an atrial event must lie in order in any way to be considered as being based on far-field detection.

The atrial events are illustrated above the horizontal center line in the diagrams. The ventricular stimulation events are illustrated below the horizontal center line.

A second condition for an atrial event being categorized as being based on far-field detection (besides the condition that the atrial event occurs in the far-field interval) is that the spacing in respect of time of the atrial event in relation to the preceding ventricular event, within narrow tolerance limits, corresponds to the spacing in respect of time of another atrial event relative to the respective preceding ventricular stimulation pulse. The spacing in respect of time between ventricular stimulation pulses and the detected atrial event—previously also referred to as the capture interval CI—is illustrated by a double-headed arrow in each of FIGS. 5a and 5b.

As, in the example illustrated in FIG. 5a, three atrial events were detected, which are both in the far-field interval (shown in gray) and also each involve practically the same spacing relative to the preceding ventricular stimulation pulse, the three atrial events which are correspondingly marked in FIG. 5a are categorized as being based on far-field detection.

The example in FIG. 5b admittedly also satisfies the condition that the corresponding atrial events are within the far-field interval, but the spacings thereof relative to respectively preceding ventricular stimulation pulses differ from each other in such a way that the atrial events are not categorized as being based on far-field detection.

That form of recognition of such atrial events which are based on far-field detection makes it possible for the post-ventricular atrial blanking time (PVAB) to be kept particularly short so that even a particularly large number of intrinsic atrial events is to be detected if atrial stimulation is ineffective, because for example the stimulation pulse strength of the atrial stimulation pulse (atrial amplitude) is less than the atrial stimulus threshold. In that case of ineffective atrial stimulation, a regular atrial rhythm is produced, independently of the atrial stimulation rhythm. That can also be seen from FIG. 5b. There, shown above the horizontal center line are both atrial stimulation events, more specifically in the form of long vertical markers, while atrial sense events are shown in the form of short wide atrial markers, in each case above the horizontal center line of the diagram.

The advantages which are to be achieved with embodiments of the present invention are thus clearly apparent from the time-event diagrams in FIGS. 5a and 5b.

What is claimed is:

1. An implantable electrostimulator for the stimulation of a heart, in particular for at least two heart chambers, said electrostimulator comprising:

at least one atrial and ventricular channel;

electrode connections which are connected to a stimulation unit for the delivery of atrial and ventricular stimulation pulses, in such a way that atrial or ventricular stimulation pulses are to be delivered by way of one or more electrode lines connected to the electrode connections;

a stimulation control unit which is connected to the stimulation unit and which is adapted to trigger the delivery of stimulation pulses and to determine the strength of the stimulation pulses and for that purpose to deliver a stimulation control signal to the stimulation unit; and a detection unit which is connected to the stimulation control unit and at least indirectly to the electrode connections and which is adapted to evaluate electrical potentials which are applied to the electrical connections and which in particular are to be intracardially recorded in order to detect intrinsic atrial events characteristic of natural contractions of an atrium, and wherein the stimulation control unit is adapted for the purposes of stimulation success checking (capture detection) in the atrium to trigger at least one atrial stimulation pulse and to detect stimulation success (capture) in the atrium or ineffective atrial stimulation (non-capture) on the basis of non-detection or detection respectively of at least one possibly occurring intrinsic (natural, spontaneous) atrial event within a predetermined period of time, and at least for a limited period of time serving in particular for stimulation success checking (capture detection) or a stimulus threshold test, to trigger ventricular stimulation pulses with the expiry of an AV interval which begins with an intrinsic or stimulated atrial event and which is so short that fusion events, that is to say events in respect of which a ventricular stimulation pulse occurs substantially at the same time as a natural ventricular contraction, are avoided, by setting the AV interval for said limited period of time to a value that is shorter than an AV interval corresponding to an intrinsic rate (SR) prior to said limited period of time or shorter than an AV interval corresponding to the stimulation rate (PR) prior to said predetermined period of time, whichever is shorter, and to distinguish atrial events which are based on far-field detection of ventricular events in the atrium from intrinsic atrial events insofar as such atrial events which are at a spacing in respect of time with respect to the respectively preceding ventricular stimulation pulse, which at least approximately corresponds to the time spacing between a ventricular stimulation pulse and the corresponding atrial event in a preceding or later cardiac cycle, are evaluated as based on far-field detection and are not counted as intrinsic events.

2. The electrostimulator as set forth in claim 1, wherein the stimulation control unit is adapted to produce a far-field signal characterizing an atrial event based on far-field detection when the atrial event detected by the detection unit occurs in a predetermined far-field coupling interval which is started from a respective ventricular stimulation pulse and which terminates at latest 150 ms after the triggering of a ventricular stimulation pulse.

3. The electrostimulator as set forth in claim 2, wherein the far-field coupling interval is started between 50 and 100 ms after triggering of the ventricular stimulation pulse and ends between 150 and 200 ms after triggering of the same ventricular stimulation pulse.

4. The electrostimulator as set forth in claim 1, wherein the stimulation control unit is adapted to set the AV time during the predetermined period of time in such a way that the AV time is so short that no fusion beats occur in the ventricle and no retrograde conductions from the ventricle to the atrium occur in the case of effective atrial and ventricular stimulation.

5. The electrostimulator as set forth in claim 4, wherein the AV interval is shorter than 200 ms and preferably is of a duration of between 100 and 130 ms.

6. The electrostimulator as set forth in claim 1, wherein the stimulation control unit is adapted to also evaluate events within a blanking time after ventricular stimulation in such a way that all those events within the blanking time are then categorized as an intrinsic event, in relation to which there does not exist any other atrial event within the predetermined period of time, which follows or followed a respectively preceding ventricular stimulation pulse with an identical or similar coupling interval.

7. The electrostimulator as set forth in claim 1, wherein the stimulation control unit is adapted to produce a retrograde stimulus conduction signal if the detection unit detects an intrinsic atrial event within a predetermined spacing in respect of time after triggering of a ventricular stimulation pulse.

8. The electrostimulator as set forth in claim 7, wherein the predetermined time spacing is a coupling interval of between 180 ms and 350 ms between triggering of the ventricular stimulation pulse and detection of the intrinsic atrial event.

9. The electrostimulator as set forth in claim 7, wherein the stimulation control unit is adapted to produce a Loss-of-Capture signal (LOC) if the ratio of the number of retrograde stimulus conduction signals to the number of triggered ventricular stimulation pulses within a predetermined period of time exceeds a predetermined threshold value of between 0.5 and 1.

10. The electrostimulator as set forth in claim 9, wherein the predetermined threshold value is 0.8.

11. The electrostimulator as set forth in claim 1, wherein the stimulation control unit is adapted to produce a crosstalk signal if the detection unit detects an intrinsic atrial event within a predetermined time window which begins with triggering of a respective ventricular stimulation pulse.

12. The electrostimulator as set forth in claim 11, wherein the predetermined time window is of a duration of between 30 ms and 70 ms, preferably 50 ms.

13. The electrostimulator as set forth in claim 11, wherein the detection unit is adapted to detect only such atrial events as intrinsic events, with which no crosstalk signal or no far-field signal is to be associated.

14. The electrostimulator as set forth in claim 1, wherein the stimulation control unit is adapted to inhibit triggering of a ventricular stimulation pulse if an intrinsic ventricular event is detected within the AV interval.

15. The electrostimulator as set forth in claim 1, wherein the stimulation control unit is adapted over a predetermined period of time including a plurality of cardiac cycles to trigger stimulation pulses at a set stimulation rate and/or in a triggered mode in such a way that stimulation pulses are not inhibited, for the predetermined period of time to detect possibly occurring intrinsic (natural, spontaneous) events, and for the predetermined period of time to ascertain the presence or absence of a natural cardiac rhythm on the basis of the detected or non-detected intrinsic (natural, spontaneous) events.

16. The electrostimulator as set forth in claim 15, wherein the stimulation control unit is adapted to derive the set stimulation rate from a rate applied prior to the predetermined period of time including a plurality of cardiac cycles, in such a way that the set stimulation rate is greater than the previously applied rate.

17. The electrostimulator as set forth in claim 15, wherein the stimulation control unit is adapted to set the stimulation rate at which the delivery of stimulation pulses is not inhibited in an inhibited mode by repeatedly increasing the stimulation rate by a predetermined value until inhibition no longer occurs.

18. The electrostimulator as set forth in claim 15, wherein the stimulation control unit is adapted to determine the stimulation rate at which the delivery of stimulation pulses is not inhibited in a triggered mode by a one-off increase in the stimulation rate by a predetermined value.

19. The electrostimulator as set forth in claim 15, wherein the electrostimulator is in the form of an atrial cardiac pacemaker, the stimulation unit is adapted to produce and deliver atrial stimulation pulses, the detection unit is adapted to detect intrinsic atrial events and the stimulation control unit is adapted to ascertain a natural atrial cardiac rhythm on the basis of intrinsic events detected by the detection unit in the atrium.

20. The electrostimulator as set forth in claim 19, wherein the stimulation control unit is adapted in the predetermined period of time including a plurality of cardiac cycles to trigger atrial stimulation pulses at a set stimulation rate in a triggered mode or at an atrial stimulation rate which is set in such a way that atrial stimulation pulses are not inhibited, and to trigger ventricular stimulation pulses at a set stimulation rate in a demand mode in which ventricular stimulation pulses are inhibited if intrinsic ventricular events are detected within a respective ventricular escape interval.

21. The electrostimulator as set forth in claim 15, wherein the stimulation control unit is adapted to ascertain the presence or absence of a natural cardiac rhythm in dependence on whether and/or how many intrinsic events are detected by the detection unit within the predetermined period of time.

22. The electrostimulator as set forth in claim 15, wherein the stimulation control unit is adapted to take account of blanking times in which possibly occurring natural events cannot be detected, for ascertaining the presence or absence of a natural cardiac rhythm.

23. The electrostimulator as set forth in claim 22, wherein the stimulation control unit is adapted, on the basis of detected natural events, taking into account non-detected natural events which potentially occurred in the blanking times, to reconstruct a natural cardiac rhythm and to produce a signal characterizing a natural cardiac rhythm if the detected natural cardiac events are to be associated with a regular natural cardiac rhythm.

24. The electrostimulator as set forth in claim 15, wherein the detection unit is adapted for each detected intrinsic event to produce a sense marker signal in relative time association with respect to the moment in time at which the event occurs.

25. The electrostimulator as set forth in claim 24, wherein the stimulation control unit is adapted, for each triggered stimulation pulse, to produce a respective pace marker signal and to ascertain the presence of a natural cardiac rhythm on the basis at least of the sense marker signals or additionally the pace marker signals.

26. The electrostimulator as set forth in claim 15, wherein the stimulation control unit is adapted to determine a stimulation control signal for stimulation strength in dependence on whether the presence or absence of a natural cardiac rhythm is ascertained within the predetermined period of time.

27. The electrostimulator as set forth in claim 26, wherein the stimulation control unit is adapted to produce a stimulation control signal which causes an increase in the pulse strength of a stimulation pulse when the presence of a natural cardiac rhythm is ascertained within the predetermined period of time.

28. The electrostimulator as set forth in claim 15, wherein the stimulation control unit is adapted to determine a capture control signal in dependence on whether the presence or absence of a natural cardiac rhythm is ascertained within the predetermined period of time and additionally or alternatively to produce a Loss-of-Capture signal (LOC) in the case of the presence of a natural cardiac rhythm within the predetermined period of time.

29. The electrostimulator as set forth in claim 15, wherein the stimulation control unit is adapted to deliver a plurality of stimulation pulses at the derived increased stimulation rate and to produce a stimulation control signal which causes an increase in the pulse strength of a stimulation pulse when within the predetermined period of time the ratio of the number of pulses delivered at the derived increased stimulation rate in relation to the number of intrinsic events detected within the predetermined period of time exceeds a predetermined value.

30. The implantable electrostimulator of claim 1 further comprising an atrial capture detector having a signal or data input for signals or data representing cardiac events, a capture control unit which is adapted to evaluate the signals or data representing atrial events over a period of time including a plurality of cardiac cycles and on the basis of data or signals representing intrinsic atrial events to ascertain the presence or absence of a natural cardiac rhythm and in the case of the presence of a natural cardiac rhythm to produce a capture signal characterizing stimulation success or in the case of the absence of a natural cardiac rhythm to produce a Loss-of-Capture (LOC) signal.

* * * * *